United States Patent [19]

Dougherty et al.

[11] Patent Number: 4,908,227
[45] Date of Patent: Mar. 13, 1990

[54] DIVINYL EPOXY ETHERS

[75] Inventors: James A. Dougherty, Prospect Park; Fulvio J. Vara, Chester; Lowell R. Anderson, Morristown, all of N.J.

[73] Assignee: GAF Chemicals Corporation, Wayne, N.J.

[21] Appl. No.: 237,489

[22] Filed: Aug. 29, 1988

Related U.S. Application Data

[62] Division of Ser. No. 109,389, Oct. 16, 1987, abandoned.

[51] Int. Cl.$^4$ ............................................. B05D 3/06
[52] U.S. Cl. ...................................... 427/44; 549/539; 549/554; 549/555
[58] Field of Search ...................... 549/539, 554, 555; 427/44

[56] References Cited

U.S. PATENT DOCUMENTS

| | | | |
|---|---|---|---|
| 3,203,939 | 8/1965 | Tinsley et al. | 549/555 |
| 3,414,634 | 12/1968 | Sorkin | 549/555 |
| 3,699,131 | 10/1972 | Wang et al. | 549/539 |
| 4,137,138 | 1/1979 | Batt et al. | 427/44 |
| 4,593,051 | 6/1986 | Koleske | 427/44 |
| 4,714,655 | 12/1957 | Bordoloi et al. | 427/44 |

FOREIGN PATENT DOCUMENTS 1023783  3/1966  United Kingdom .

Primary Examiner—Stanley Silverman
Attorney, Agent, or Firm—Marilyn J. Maue; Joshua J. Ward

[57] ABSTRACT

This invention relates to divinyl epoxy ethers having the formula

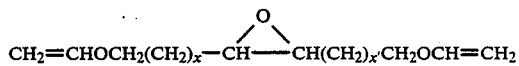

wherein x and x' are integers each having a value of from 0 to 3 and to the preparation and use of the above divinyl epoxy ethers for metal, wood or plastic coatings which possess high resistance to solvents and improved flexibility over saturated epoxy compounds.

9 Claims, No Drawings

DIVINYL EPOXY ETHERS

This is a division of U.S. patent application Ser. No. 109,389, filed Oct. 16, 1987 now abandoned.

In one aspect this invention relates to novel compounds of the vinyl epoxy ether type.

In another aspect the invention relates to the preparation of said vinyl epoxy ethers and in a third aspect the invention pertains to the use of said vinyl epoxy ethers in an adhesive coating formulation.

BACKGROUND OF THE INVENTION

Many formulations have been proposed for coating metal and plastic surfaces, including polyepoxy compounds such as the cycloaliphatic diepoxides, monoepoxides and glycol ethers. These compounds are generally formulated in solvents or emulsified with water and reacted with typical epoxy hardeners such as epoxy polyamides, polyamines, anhydrides, melamines, imidazoles and acids. However, these formulations pollute the atmosphere since the solvent must be evaporated in order to form a usable coating. The alternative of solvent recovery is found to be uneconomical and therefore not widely practiced. Water emulsified epoxy coatings also require evaporation which, due to the high heat of water vaporization, is also uneconomical and difficult to drive to completion. To avoid these disadvantages, the use of a solvent free coating formulation comprising a cross-linkable base resin, a cycloaliphatic epoxy diluent and a cross-linking initiator has been proposed. Although such a formulation would be acceptable from an economical and environmental standpoint, it is known that the cycloaliphatic epoxy compounds react slowly with the polyepoxy resin resulting in a lack of resistance to common polar solvents such as methyl ethyl ketone, acetone, alcohols, etc. Still further, the polyepoxy compounds produce brittle coatings unless substantial amounts of a flexibilizing agent, such as tripropylene glycol is added to the formulation.

Another deficiency of the above formulated compounds is their inability to accept high levels of pigment loading before an unmanageable viscosity is reached.

Accordingly, it is an object of this invention to overcome the deficiencies of the prior coatings described above.

Another object of this invention is to provide an adhesive protective coating suitable for thin layer application which shows high resistance to chemical solvents.

Still another object of the invention is to provide a formulation which will accept a high level of pigment loading and which possesses good wear resistance for lettering and designs.

Still another object is to provide a formulation which possesses wear and slip resistance for lettering and/or decorative designs which may be imprinted on the surface of a substrate over which the formulation is coated.

Another object is to provide an economical and commercially feasible method for preparing the compounds of the present invention.

Yet another object is to provide new and novel compounds.

THE INVENTION

According to this invention there is provided novel compounds having the formula

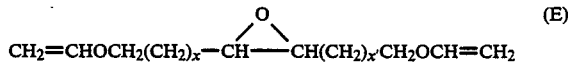

wherein x and x' are integers each having a value of from 0 to 3.

Of the above compounds, epoxy butanediol divinyl ether is most preferred.

The compounds of this invention are prepared by a transvinylation reaction according to the general formula

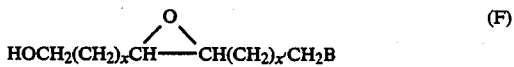

+ a coreactant high boiling mono- or polyvinyl ether reactant having the structure G or H.

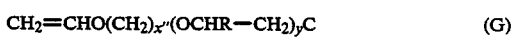

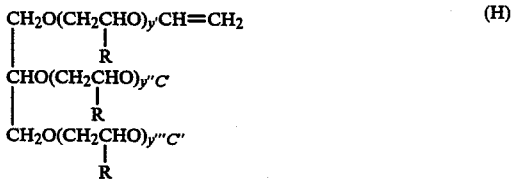

wherein B is —OH or —OCH=CH$_2$; C, C' and C" are each hydrogen, C$_1$ to C$_4$ alkyl, C$_1$ to C$_4$ alkoxy or —(CH$_2$)$_{x''}$OCH=CH$_2$ when B is —OCH=CH$_2$ and C and at least one of C' and C" are —(CH$_2$)$_{x''}$OCH=CH$_2$ when B is hydroxyl; x" is an integer having a value of from zero to 3; R is hydrogen or methyl; y is an integer having a value of from 3 to 5; y', y" and y''' are integers the sum of which is from 4 to 24, and x and x' are integers having a value of from 0 to 3. In compound (H) it is essential that the vinyl groups be separated by more than 4 carbon atoms. If they are not, the monovinylated compound may undergo internal addition of the hydroxy group to the vinyl group and form a 5 or 6 membered ring; thus failing to provide the divinylated compound and destroying the cross-linking potential of the vinyl group.

The alcoholic epoxy reactant (F) is mixed with the vinyl ether coreactant (G) or (H) in an amount at least sufficient to convert all of the hydroxy sites in compound (F) to vinylether groups. More specifically, a ratio of hydroxy group to vinyl ether group between about 1:1 and 1:5, preferably 1:1.5 to 1:3 for each hydroxylated site in reactant (F) at which transvinylation is to be effected can be employed. These coreactants are required to have low volatility so that they will not be vaporized under the ensuing reaction conditions. Preferred coreactants have a volatility less than 55° C. at 1.5 mm Hg and a boiling point greater than 250° C. A soluble mercury salt catalyst, between about 1 and about 10% of the total mixture is added to initiate the reaction. Although mercuric acetate is the preferred catalyst, other mercury compounds such as mercuric sulfate, mercuric nitrate, and mercuric chloride may be substituted in whole or in part to induce cross-linking. The resulting mixture is then reacted at a temperature between about 25° C. and 250° C., preferably between about 60° C. and about 150° C. and below the decomposition temperature of the epoxide and then vacuum distilled. The distillation pressures employed may range between about 0.5 and about 50 mm Hg, preferably between about 1 and about 10 mm Hg.

In a batch process, the reaction is conducted over a period of from about 1 to about 3 hours; however, the process may be carried out under continuous conditions or with intermittent product removal. In either case the product draw-off shifts the equilibrium of the product lean reaction mixture to the production of more product.

Thus, to maximize product yield, the distillation can be halted and the reaction mixture allowed to re-equilibrate for about 5 to 30 minutes, after which the distillation and product take-off is resumed and additional product collected. This operation can be repeated as many times as desired to drive the reaction toward completion.

The desired product and a small amount of hydroxy ether by-product withdrawn from the reaction zone is subjected to closely controlled fractional distillation using from 10 to 30 plates, preferably from 12 to 25 plates under vacuum and at a temperature between about 40° C. and about 100° C. Close temperature control is particularly important in the production of each of the divinyl epoxy ethers since there is a very small difference in boiling point between the product and the unreacted alcohol component.

The reaction for the most preferred product of this invention may be represented as follows.

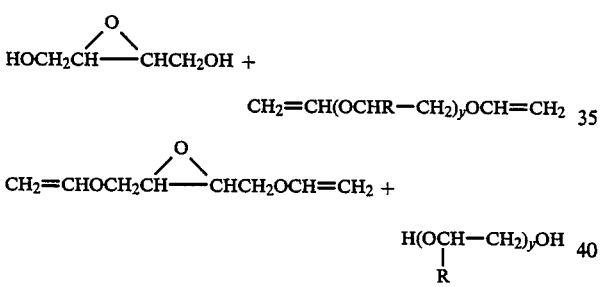

wherein the mole ratio of the epoxydiol to the divinylated coreactant is between about 1:1 and about 1:2.

The more general reaction can be expressed by the equation:

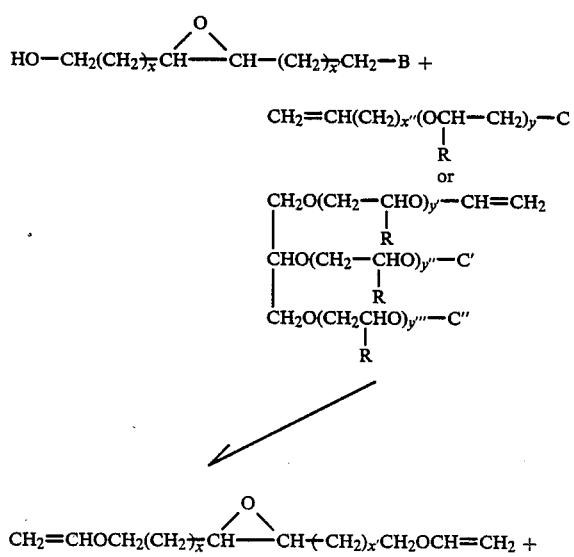

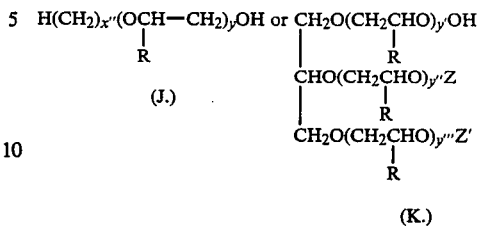

wherein each of Z and Z' is independently vinyl, hydroxy, or the same as C' and C'' depending on the transvinylation (—OH) sites in the alcoholic reactant (F) and the terminal groups in the coreactant (H) and B, C, C', C'', R, x, x', x'', y, y', y'' and y''' are as defined above.

The product of the above reaction is obtained in at least 80% purity and can be further purified by extraction with a polar solvent or selective solubilization of by-product with for example, ether, followed by evaporation. In the most preferred embodiment, the divinyl epoxy co-reactant is a liquid having low volatility, for example less than 1.5 mm Hg at 55° C. and a boiling point greater than 250° C.

Although purification of product may be required for some uses, e.g. in medicinal or cosmetic uses, removal of by-product to levels below about 15% is usually not required. Accordingly, the product obtained from the fractional distillation of the transvinylation reaction can be directly formulated into a composition suitable for coating metal or plastic surfaces. As can be seen from the product structural formula, the present compounds have high cross-linking capability which takes place at both the vinyl and epoxy sites. A surface protected with this compound in the formulation is provided with a pigment loadable coating which can be used on plastic food bags or metal cans and one which is resistant to solvent deterioration. These coatings also protect against metal corrosion and moisture penetration. Another advantage realized by the incorporation of the present vinyl epoxy ethers is their ability to impart flexibility to the coating material so that no extraneous flexibilizing agent need be added to the coating composition. This represents an improvement over coatings employing saturated epoxides.

Generally coating compositions of the present invention include between about 30 wt. % and about 55 wt. % of the present compound; between about 65 wt. % and about 45 wt. % of an adhesive base resin such as an epoxy resin or a cyclo aliphatic epoxide; between about 0.5 wt. % and about 6 wt. % of a cross-linking initiator and between about 0 and about 3 wt. % of a surfactant. The base resins of the present compositions are cross-linkable components which impart adhesion and hardness to the composition and are preferably those which contain one or more epoxy and/or olefinically unsaturated groups. Suitable examples of such compounds include diglycidyl ethers of bisphenol A having an epoxy equivalent weight between about 150 and about 10,000, polyglycidyl ethers of phenol formaldehyde resin (novolac), and cycloaliphatic epoxides, and the like. Those which contain olefinic unsaturation include unsaturated polyesters and polyethers.

The present compound is mixed at room temperature under atmospheric pressure with the adhesive base resin in a mole ratio of between about 20:80 and about 80:20, preferably in a mole ratio of from about 35:65 to about 65:35 until a homogeneous mixture is obtained. The surfactant and the photoinitiator are then added to the resulting mixture which can be then coated on a surface such as a surface of aluminum, steel, chromium, copper, tin-plate, brass, bronze, tin-free steel as used in cans for beer or beverages or on a plastic substrate such as a surface of polyester, polystyrene, acrylic and methacrylic polymer and the like.

Suitable photoinitiators used to induce cross-linking between the vinyl epoxy ether and the base resin include triphenyl sulfonium hexafluorophosphate, fluoroarsenate, fluoroammoniate, diazonium salts, aryl ferrocene and fluorophosphate. Generally, for radiation curing, deblockable acids such as onium salts, iron-arene complexes or para-toluene sulfonic acid complexes can be employed as cross-linking initiators. Specific initiators for electron beam curing are illustrated in the following Table A.

For UV curing, sulfonium salts may be employed. Structural features associated with the cationic portion of the photoinitiator determine its absorption characteristics, its photosensitivity, and ultimately, the rate of generation of the initiating acidic species. In the polymerization of the present divinyl ether monomers where the rates of both initiation and propagation are very rapid, the overall rate of UV-cure will be determined by the photosensitivity of the particular photoinitiator used. Altering the structure of the cation by introduction of appropriate chromophors on the aromatic rings can affect the cure rates. A comparison between the UV-cure rates of diethylene-glycol divinyl ether using three different triarylsulfonium salts having identical anions but varying in the structure of their cations is shown in Table B. For the same molar concentration of photoinitiators, the diphenyl-[(4-phenylthio)phenyl] sulfonium salt, V, is considerably more efficient in cationic polymerization of the present divinyl ether monomers than other triarylsulfonium salts, due to its better UV absorption characteristics.

TABLE A

ELECTRON BEAM CURE SPEED OF DIETHYLENE GLYCOL DIVINYL ETHER (DEGDVE) IN THE PRESENCE OF VARIOUS CATALYSTS

| Catalyst (2 M soln. in DEGDVE) | Maximum Conveyor Speed for Tack-Free Coating (ft/min) | Minimum Energy Dose for Tack-Free Coating[a] (Mrads) |
|---|---|---|
| 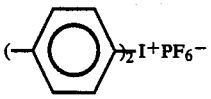 | 235[b] | <0.10 |
| 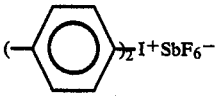 | 235[b] | <0.10 |
| 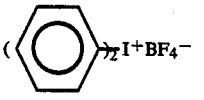 | 235[b] | <0.10 |
| $Ar_3S^+SbF_6^-$ | 68 | 0.32 |
| $Ar_3S^+PF_6^-$ | 68 | 0.32 |
| 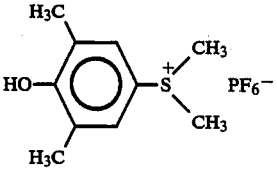 | 68 | 0.32 |
| 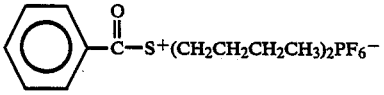 | 102 | 0.21 |
| $(CH_3CH_2)_3S^+PF_6^-$ | 85 | 0.26 |

[a]Beam Current = 0.32 ma
[b]Maximum Conveyor Speed of CB-150

TABLE B

| Photoinitiator (0.001 mole/100 g DEGDVE) | $\lambda_{max}(\epsilon)$ in methanol | Cure Rate (ft/min)[a] |
|---|---|---|
| III  (C₆H₅)₃S⁺ AsF₆⁻ | 230 nm (17,500) | 300 |
| IV  triphenylsulfonium-type with O bridge, AsF₆⁻ | 238 (19,900)<br>292 (5,000) | 150 |
| V  C₆H₅—S—C₆H₄—S⁺(C₆H₅)₂ AsF₆⁻ | 225 (23,400)<br>300 (19,500) | 500 |

[a] One Hanovia 200W mercury arc lamp

Another means of increasing the efficiency of cationic photoinitiators is by the use of photosensitizers. These compounds absorb light in a region of the spectrum in which the photoinitiator is transparent and then transfer that energy to the photoinitiator, inducing its photolysis. In addition to improving the overall efficiency of these photoinitiators by increasing their effective light absorption, photosensitizers make it possible to carry out the photopolymerization of the multifunctional vinyl ethers using visible light. For example, a solution of 0.5% triphenylsulfonium hexafluorophosphate in diethyleneglycol divinyl ether containing 0.05% perylene will cure to a tack-free 2 mil film in 5 seconds when exposed to a G.E. DWY photoflood lamp. The emission of this lamp lies entirely in the visible region. However, when perylene is omitted, no curing is observed even after 1 minute irradiation.

For thermoset curing, boron trifluoride complexes, para-toluene sulfonic acid complexes and trifluoromethane sulfonic acid complexes are particularly recommended.

The composition containing the present vinyl epoxy ether, the base resin, the cross-linking initiator and optionally surfactant, is coated on a substrate in a thickness between about 0.02 and about 30 mils, preferably between about 0.1 to 3 mils and most preferably between about 0.2 to 1 mil. In radiation curing, the coated substrate is cured to a track-free state at an energy for light radiation of between about 0.15 joules/cm² and about 225 joules/cm², preferably between about 6 joules/cm² and about 105 joules/cm². For electron beam radiation, an energy of between about 0.1 and about 5 megarads is employed. Any source of radiation curing can be employed for the present process.

After the tack-free state is achieved, the curing is completed by a post-bake for a period of from about 2 to about 20 minutes at a temperature of from about 50° to about 200° C., preferably from about 5 to about 15 minutes at a temperature of from about 125° to about 175° C. Alternatively, curing can be effected at a temperature of between about 25° C. and about 35° C. Alternatively, curing can be effected at a temperature of between about 25° C. and about 35° C. for a period of from about 3 to about 14 days, preferably from about 6 to about 9 days.

When curing speed is not important, a thermoset process can be employed. In this process, merely heating to between about 25° C. and about 250° C., preferably between about 50° C. and about 200° C., for a period of 5 to about 30 minutes in the presence of a Lewis acid, e.g. trifluoromethyl sulfonic acid or any of those mentioned above, is sufficient to provide a tack-free protective coating.

The present formulations function as reactive diluents when used with printing ink, pigment and the like. These coloring materials are uniformly dispersed in the coating mix, applied in a predetermined pattern in one or more colors and in one or more applications and then subjected to curing as described above. During curing the coating is internally cross-linked which involves bonding between epoxy and vinyl, vinyl and vinyl and vinyl and hydroxy. Under optimum conditions with preferred initiators, the present composition is capable of immediate cure such that 700 feet per minute of film can be cured to a tack-free condition. Such rapidity in curing represents a great improvement over prior UV curable compositions which require at least 1 minute per 100 feet of film. One of the principal advantages of the vinyl ethers of this invention over others is their resistance to common solvents including ketones, alcohols, esters and aromatic solvents. This property makes them useful in any coating formulation including radiation cured or heat cured coatings.

Having thus generally described the invention, reference is now had to the following Examples. However it is to be understood that the scope of this invention is not intended to be limited to these embodiments but is extended to the general discussion above with modifications and alterations normally apparent to the skilled artisan and to the appended claims.

EXAMPLE 1

Into the pot of a 15 plate Oldershaw distillation column was introduced 52 g. of epoxybutanediol, 115 g. of triethylene glycol divinyl ether, $$CH_2=CHO(CH_2CH_2O)_3CH=CH_2$$

and 10 g. of mercuric acetate. The mixture was heated to a pot temperature of 85° C. for a few minutes and a first cut of 12.6 g. of product having the formula.

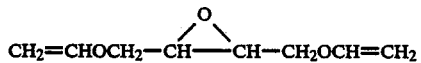
$$CH_2=CHOCH_2-CH\overset{O}{-\!\!-\!\!-}CH-CH_2OCH=CH_2$$

was distilled off and collected in a few minutes within a 3° temperature range including 68° C. under a pressure of 1.5 mm Hg. The product was obtained in 76.6% purity and contained a minor amount of by-product having the formula $H(OCH_2CH_2)OH$. The product was identified by gas chromatography, NMR and infrared spectrum.

To maximize product yield, the distillation can be halted and the reaction mixture allowed to re-equilibrate for the formation of additional product. The distillation and product take-off is then resumed and additional product collected. Re-equilibration can be repeated as many times as desired to maximize product yield.

EXAMPLE 2

Example 1 is repeated, except that the 200 g. of the propoxylated coreactant $$CH_2=CH(OCH_2CH)_5OCH=CH_2$$
$$\phantom{CH_2=CH(O}|\phantom{CH_2CH)_5OCH=CH_2}$$
$$\phantom{CH_2=CH(OCH_2CH}CH_3$$

is substituted therein. The same product as in Example 1 in about the same amount and purity is obtained. The by-product in this case is the corresponding propoxylated diol derivative, $$H(OCH_2CH)_5OH,$$
$$\phantom{H(O}|$$
$$\phantom{H(OCH_2}CH_3$$

EXAMPLE 3

Example 1 is repeated, except that 65 g. of mono-vinylated epoxybutanol having the formula

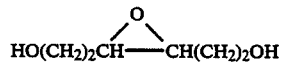
$$HOCH_2CH\overset{O}{-\!\!-\!\!-}CHCH_2OCH=CH_2$$

is reacted with 350 g. of an ethoxylated mono vinyl glycerol having the formula $$CH_2O(CH_2CH_2O)_4CH=CH_2$$
$$|$$
$$CHO(CH_2CH_2O)_4H$$
$$|$$
$$CH_2O(CH_2CH_2O)_4H$$

The same product in about the same amount and purity as in Example 1 is obtained. The by-product in this case is the corresponding ethoxylated glycerol derivative.

EXAMPLE 4

Example 1 is repeated except that 66 g. of the epoxydiol

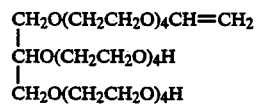
$$HO(CH_2)_2CH\overset{O}{-\!\!-\!\!-}CH(CH_2)_2OH$$

is substituted for 52 g. of the epoxybutanediol. The distillation product of the reaction, $$CH_2=CHO(CH_2)_2CH\overset{O}{-\!\!-\!\!-}CH(CH_2)_2OCH=CH_2$$

is obtained in at least 70% purity and the by-product of the reaction is the same as that obtained in Example 1.

EXAMPLE 5

Two commercial coating formulations (No. 1 and No. 2) and a formulation of the present invention (No. 3) were prepared and compared. The components of these compositions are shown in following Table I.

All amounts are reported as wt. %.

TABLE I

| COMPOSITION NO. 1 | | COMPOSITION NO. 2 | | COMPOSITION NO. 3 | |
|---|---|---|---|---|---|
| 52% | cycloaliphatic epoxide (1) | 53.7% | divinyl compound (6) | 47.3% | vinyl epoxy ether (7) |
| 18.5% | Bisphenol A epoxide (Epon-834) (2) | 42.3% | bisphenol A epoxide (Epon-834) | 48.2% | bisphenol A epoxide (Epon-834) |
| 25% | tripropylene glycol (3) | 3.5% | sulfonium salt initiator (4) | 4.0% | sulfonium salt initiator (4) |
| 4.0% | sulfonium salt initiator (4) | 0.5% | fluorochemical surfactant (5) | 0.5% | fluorochemical surfactant (5) |
| 0.5% | fluorochemical surfactant (5) | | | | |

(1) 3,4-epoxycyclohexylmethyl-3'4'-epoxycyclohexane carboxylate (cross-linking agent)
(2) an epoxy resin based on bisphenol A having an epoxy equivalent weight between about 180 and 6,000 (provides adhesion & strength)
(3) this composition required a substantial amount of flexibilizer to prevent cracking
(4) triphenyl sulfonium hexafluorophosphate
(5) fluorinated alkyl alkoxylates (Fluorochemical 171 supplied by Minnesota Mining & Manufacturing Co., St. Paul, Minnesota)
(6) triethylene glycol divinyl ether cross-linking agent
(7) epoxy butanediol divinyl ether cross-linking agent of Example 1

The above formulations were individually coated on aluminum panels by hand draw-down using a number 3 Mayer bar to give a coating thickness of about 6.5 microns. The panels were then subjected to a UV light exposure of 15 joules/cm² by passing them under two 200 watt/inch UV lamps at 100 feet/minute. This was followed by a thermal bake at 177° C. for 10 minutes. The coatings were then subjected to a Cross-Cut Tape Test (ASTM D-3359-K-B), a Boiling Water Immersion Test and a solvent resistance test. For the water immersion, the coated panel was immersed in boiling water for 30 minutes, after which it was removed, dried and subjected to adhesion test ASTM D-3359-K-B.

For the solvent resistance test, a methylethyl ketone saturated cheesecloth was rubbed across the surface of the coated panel under a constant pressure. The number of back and forth strokes needed to break through the coating was recorded. The results of these tests are reported in following Table II.

TABLE II

| TEST | COMPOSITIONS | | |
|---|---|---|---|
| | 1 | 2 | 3 |
| Adhesion | 100 | 100 | 100 |
| Water Submersion | 100 | 100 | 100 |
| Solvent Resistance | 2 | 23 | >200 |

In addition to the above results, it was found that Composition No. 3 was significantly less viscous than Composition 1. Accordingly, thin films of the type shown in Composition 3, suitable for coating magnetic tapes and other recording media, could be produced. This property, together with the increased flexibility and solvent resistance of the compositions incorporating the present divinyl epoxy ethers render them excellent candidates for coating electron beam recording films and wire like filaments.

EXAMPLE 6

Example 5 was repeated with the same formulations except that the percent sulfonium salt initiator was reduced to 1.5 wt. % (Compositions 4, 5 and 6 below corresponding to 1, 2 and 3 respectively). Coatings of 6.5 microns were applied to aluminum panels as in Example 5 and were cured by an electron beam exposure of 1.5 Mrad. After a thermal bake of 10 minutes at 177° C. panels were subjected to the same tests as set forth in Example 5. The results are as reported in Table III.

TABLE III

| Test | Composition | | |
|---|---|---|---|
| | 4 | 5 | 6 |
| Adhesion | 100 | 100 | 100 |
| Water Submersion | 100 | 100 | 100 |
| Solvent Resistance | 4 | 50 | >200 |

EXAMPLE 7

Example 5 was again repeated with the same formulations except that the sulfonium salt photoinitiator was replaced with 1.5 wt. % of the diethylammonium salt of trifluoromethanesulfonic acid (Compositions 7, 8 and 9 below corresponding to 1, 2 and 3 respectively). Coatings of 6.5 micron were applied on aluminum panels as in Example 5, were cured with a thermal bake of 15 minutes at 177° C. and the coatings subjected to the same tests as in Example 5. The results are as reported in following Table IV.

TABLE IV

| Test | Composition | | |
|---|---|---|---|
| | 7 | 8 | 9 |
| Adhesion | 100 | 100 | 100 |
| Water submersion | 100 | 100 | 100 |
| Solvent resistance | 3 | 25 | >200 |

Many alterations and variations of the above description and disclosure will become apparent to those skilled in the art. However, it is intended that such modifications and alterations be included within the scope of this invention.

What is claimed is:

1. The process of formulating a coating containing a cross-linkable base resin, a cross-linking initiator and an effective cross-linking amount of an epoxy divinyl ether compound having the formula

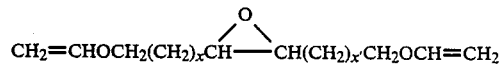

wherein x and x' each independently have a value of from 0 to 3 and coating said formulation on a substrate.

2. The process of claim 1 wherein said formulation is coated on substrate in a thickness of between about 0.02 mil and about 30 mil and is cured thereon at a temperature of between about 25° C. and about 250° C.

3. The process of claim 2 wherein said formulation is coated on a metal substrate in a thickness of between about 0.5 mil and about 5 mils and is cured thereon at a temperature of between about 50° C. and about 200° C.

4. The process of claim 1 wherein said coating is cured on the substrate by exposure to a source of radiation or heat.

5. The process of claim 1 wherein said coating is cured on the substrate by exposure to an electron beam at from about 0.5 to about 5 megarads.

6. The process of claim 4 wherein said coating is cured by exposure to UV light at between about 0.15 joules/cm$^2$ and about 225 joules/cm$^2$.

7. The process of claim 6 wherein said coating is cured at between about 6 joules/cm$^2$ and about 150 joules/cm$^2$.

8. The process of claim 1 wherein x and x' in said epoxy divinyl ether have a positive value.

9. The process of claim 1 wherein x and x' in said epoxy divinyl ether are zero.

* * * * *